United States Patent [19]
Lihl et al.

[11] Patent Number: 5,299,481
[45] Date of Patent: Apr. 5, 1994

[54] CARRIER ARM SEAL FOR A MICROTOME OF ULTRAMICROTOME

[75] Inventors: Reinhard Lihl; Anton Lang, both of Vienna, Austria

[73] Assignee: Leica Aktiengesellschaft, Vienna, Austria

[21] Appl. No.: 954,392

[22] Filed: Nov. 6, 1992

Related U.S. Application Data

[63] Continuation of Ser. No. 755,056, Sep. 5, 1991, abandoned.

[30] Foreign Application Priority Data

Sep. 11, 1990 [DE] Fed. Rep. of Germany ....... 4028806

[51] Int. Cl.⁵ ............................................. G01N 1/28
[52] U.S. Cl. .................................. 83/170; 83/915.5; 62/320
[58] Field of Search ............ 83/915.5, 170, 171, 83/169, 648, 699; 62/320, 321, 48.1

[56] References Cited

U.S. PATENT DOCUMENTS

| | | | |
|---|---|---|---|
| 3,204,424 | 9/1965 | McCormick et al. | 83/170 X |
| 3,680,420 | 8/1972 | Blum | 83/171 X |
| 3,763,731 | 10/1973 | Wistedt | 83/915.5 X |
| 3,828,571 | 8/1974 | Lechner | 83/915.5 X |
| 3,828,641 | 8/1974 | Sitte | 83/915.5 X |
| 4,532,838 | 8/1985 | Soderkvist | 83/915.5 X |
| 4,589,203 | 5/1986 | LeDiouron | 62/320 X |
| 4,594,929 | 6/1986 | Behme et al. | 83/915.5 X |
| 4,918,941 | 4/1990 | Hagler | 83/915.5 |
| 5,048,300 | 9/1991 | Lihl | 83/915.5 X |

*Primary Examiner*—Rinaldi Rada
*Attorney, Agent, or Firm*—Bean, Kauffman & Spencer

[57] ABSTRACT

A microtome, or an ultramicrotome having the specimen arm operating through an opening in the cryo chamber wall in a manner substantially free of the mechanical influence of a conventional seal is disclosed. An elongated slot permits movement of the specimen arm while minimizing the clearance between the sides of the arm and chamber wall reduces loss. Inner and outer baffles can be used to further reduce loss.

18 Claims, 3 Drawing Sheets

CARRIER ARM SEAL FOR A MICROTOME OF ULTRAMICROTOME

This is a continuation of copending application(s) Ser. No. 07/755,056 filed on Sep. 5, 1991 now abandoned.

BACKGROUND OF THE INVENTION

The invention relates to a microtome, in particular an ultramicrotome and specifically the seal which prevents escape of the cryogen contained inside the freezing chamber through the opening of the freezing chamber wall where the specimen carrier arm is guided through.

For cryogenic preparation of samples, in particular biological samples which are subject of microscopic or electron microscopic examinations after preparation, it is necessary to maintain both sample and knife at a low temperature during preparation. Cryogenic sample preparation is typically therefore performed in a microtome or ultramicrotome attached freezing chamber which typically is accessible from the top and in which a desired low temperature is provided by introduction of a gaseous cryogen. In order to hold the temperature consistent and to avoid penetration of damp air from above into the freezing chamber, it is necessary to continuously introduce cryogen.

For the production of thin and ultra-thin slices at low temperature a tool such as a knife is commonly attached to the bottom of the freezing chamber and the specimen to be cut is attached to a carrier arm, which is moveable upwards and downwards relative to the stationary knife. To obtain precision cuts, it is necessary to have at least two requirements:
 a) the carrier arm must have a very rigid configuration; and
 b) the movement of the carrier arm during the cutting procedure cannot influence the atmosphere of the freezing chamber, in particular by allowing large amounts of cryogen to escape and causing a change of temperature inside the freezing chamber.

Unfortunately, it is difficult to design a carrier arm capable of holding and maneuvering a specimen inside the freezing chamber, which extends and is driven outside of the freezing chamber, and that complies with the above requirements.

There have been several attempts to solve this problem. For example, it is known to design the carrier arm like a bridge so that the arm reaches in an U-shape over the edge of the freezing chamber and the specimen is held at the low end of the U of the carrier arm inside the freezing chamber (so-called Christensen Bridge; U.S. Pat. No. 3,680,420). This configuration has the disadvantage that the arm, because of its U-shape, tends to lose its original shape, and has the tendency, particularly during operations involving increased cutting force, to deform, resulting in decreased cut quality. A similar design was disclosed in co-pending U.S. patent application No. 07/523,054.

According to another solution, the carrier arm is introduced through an opening into the chamber. The opening is excessively large to allow for the up and down movement of the carrier arm necessary for the cutting process. To avoid escape of cryogen, the edge of the opening is sealed to the carrier arm by means of a very thin and flexible membrane (DE-PS 1,622,996). The disadvantage of this design is the fact that the cold membrane exerts unwanted forces on the carrier arm, which has a disturbing influence on the up and down movement of the carrier arm and thus negatively influences the quality of the cut.

In another known design which introduces the carrier arm through an opening in one of the freezing chamber walls, the opening is configured as a "maze" where a number of disc shaped members located on the carrier arm extend into separate chambers for each membrane (U.S. Pat. No. 4,918,941). The membranes are moveable in the direction of the carrier arm. The membranes are arranged at the outside of the end of the carrier arm and moveable in its direction. Contact of the membranes with the respective chamber wall cause unwanted forces to occur during vertical movement of the carrier arm, resulting in vibration of the carrier arm and therefore negatively influencing the quality of the cut.

One object of the present invention is to provide a seal for the carrier arm of a microtome or ultramicrotome, which does not adversely influence movement of the carrier arm, yet at the same time prevents excess escape of cryogen, thereby maintaining the chamber atmosphere.

SUMMARY OF THE INVENTION

The present invention is related to a sample carrier arm for cryogenic sample preparation chambers such as microtomes or ultramicrotomes. In particular, the invention relates to carrier arms that are introduced through an opening in one of the freezing chamber walls. In accordance with the present invention, the carrier arm never contacts the freezing chamber wall, even during the movements during the cutting operation. The side of the carrier arm is always separated from the freezing chamber wall by a vertical air slit or gap. To preclude escape of excess cryogen through this air slit, the slit is configured as narrow and small as possible, whereas the length of the air slit measured in the direction of the flow of cryogen through the chamber is as large as possible. The invention is based on the finding that, by designing the slit to have a narrow gap between the freezing chamber wall and carrier arm, and designing the slit in the direction perpendicular to this vertical slit to be as long as possible, resistance to gaseous flow through the slit is increased. Thus, the resistance to flow is primarily determined by the width of the air slit. Therefore, it is desirable to design the width of the slit on the sides of the carrier arm, which moves upwardly and downwardly during the cutting process, to be as small as possible, while the length of the slit is relatively unimportant.

Since the carrier arm needs clearance at the top and bottom of the slit to allow upward and downward movement, at any one time during cutting, there will be a slightly wider gap at either the top or bottom (or both) of the vertical slit. To prevent excess escape of cryogen, the invention provides various alternatives which have the effect of reducing the length of the air slit and/or the air slit diameter.

The specimen arm usually has a generally uniform cylindrical cross-section and the gap between the sides of the specimen arm and the slot in the freezing chamber wall is in the range of 0.5 to 15 mm. Preferably, the gap is less than 5 mm and a gap of 1 mm is most preferred. The slot in the wall of the freezing chamber is vertically elongated to permit the necessary up and down motion of the specimen arm for specimen cutting. The vertical dimension of the gap must be sufficient to accommodate the maximum vertical movement of the specimen arm and preferably has a configuration at the top and bottom end corresponding to the shape of the specimen arm.

In another embodiment of the invention, the carrier arm is divided into various, parallel arm sections having predominantly flat side surfaces, located adjacent one another, each parallel arm section feeding through its own slit-shaped opening of the freezing chamber wall. Consequently, the predominantly flat side surfaces of each section of carrier arm maintain the desired minimum width of air slit during the up and down movement of the carrier arm, and the openings for allowing clearance, as described above, may be made relatively smaller. The result is that the clearance of these slots during up and down movement and despite the plurality of slots, only a relatively small quantity of cryogen can escape.

In a preferred embodiment of the invention, the length of the air slit is blocked by enlarging the surface of the carrier arm in the area of the opening generally perpendicular to the longitudinal axis of the carrier arm and by means of a projecting over-hand, so that the projecting overhang overlaps the openings of the freezing chamber walls. For example, a disc-like element or baffle may be rigidly attached to the carrier arm so that the disc-like element extends generally perpendicular to the longitudinal axis of the carrier arm and generally parallel to the pivot axis of the specimen. The device may be further improved by shaping the surface of the disc-like member to be complimentary to the shape of the freezer chamber wall or vice versa. Consequently a very small air slit may be maintained, even during up and down movement of the carrier arm. For example, the surfaces determining the air slit can be curved cylindrically, so that the axis of the curvature faces together with the pivot axis of the carrier arm.

The curve of the surfaces which determine the air slit do not necessarily have to create an air slit having an even and consistent width. In fact, expanding spaces may be provided in the flow direction. Expanding areas may be formed, for example, by shaping at least one of the surfaces which determine the air slit in a polygonal shape.

In addition, the disc elements described above, located perpendicular to the carrier arm, need not be only located on one side of the freezing chamber wall, but instead may be located both inside and outside the freezing chamber. The size of the air gap between the baffle and chamber wall provide for horizontal movement of the carrier arm, can easily be held under 1 mm because normal cutting feeds are in the range of 50 Å to 1 μm and the total feed range for the specimen is only 50-200 μm. The total range of the return traverse which prevents contact of the specimen with the knife after the cutting process is also 50-200 μm. It has been proven that with an air gap clearance below 1 mm, escape of cryogen through the air slit can be greatly reduced. To provide for adjustment of the air slit, the disc-like member may be designed to be axially adjustable with respect to the carrier arm.

BRIEF DESCRIPTION OF THE DRAWINGS

The nature and mode of operation of the present invention will now be more fully described in the following detailed description taken with the accompanying drawings in which:

FIG. 5b is a top view of the embodiment illustrated in FIG. 5a; and

DETAILED DESCRIPTION

Figure 1:
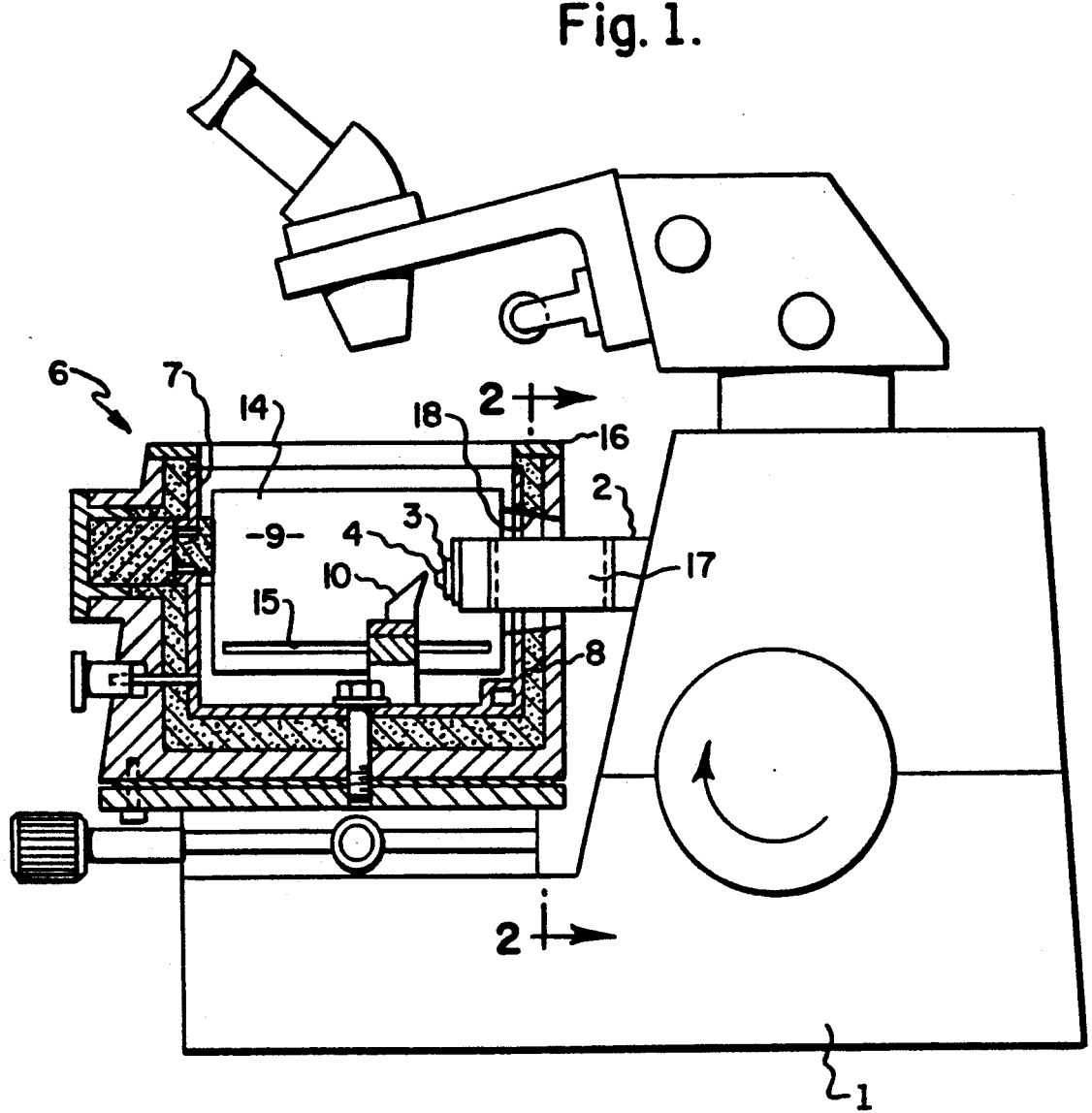
FIG. 1 is a side view of an ultramicrotome, partly sectioned in the freezing chamber area to show the inlet of carrier arm through the wall of freezing chamber.

Reference is now made more particularly to FIG. 1, wherein an ultramicrotome 1 having a carrier arm 2 is illustrated. A specimen arm 3 is shown having a specimen holder at the front end adapted to hold a specimen 4 to be prepared. A freezing chamber 6 is attached to the ultramicrotome 1. The freezing chamber typically is shaped like a box and generally includes an inner wall 7 made of a good heat conducting material and a layer 8 of heat insulating material located around the outside of the inside wall 7. On the interior of the freezing chamber 6 is an inside space 9 containing a knife 10, located so that it can produce cuts in a specimen by upward and downward movement of the specimen 4 relative to the knife 10. The configuration and function of the ultramicrotome 1 concerning this cutting process is commonly known and not part of this invention. Therefore, no further explanation of this procedure is necessary.

Figure 2:
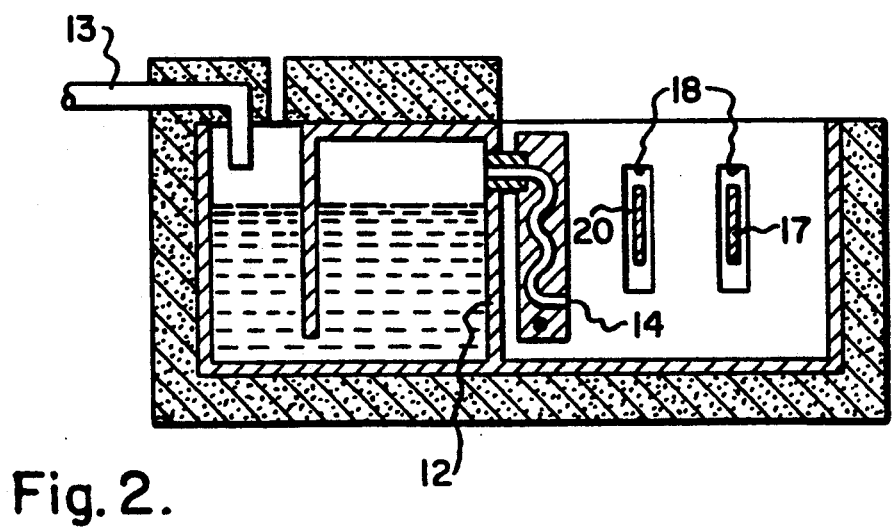
FIG. 2 is a sectional view taken along line 2—2 in FIG. 1.

As best seen in FIG. 2, on one side of the freezing chamber 6 a reserve tank 12 is provided for a liquid, which preferably is liquid nitrogen (LN). Tank 12 is covered on top by a layer of heat insulating material. When necessary, the tank 12 can be refilled through a filling inlet line 13. Reserve tank 12 extends the entire width of the freezing chamber and carries on the freezing chamber facing sidewall an outlet line 14. Line 14 feeds evaporating, gaseous nitrogen from the LN-reserve to the freezing chamber through a slit 15. The continuous gas flow into the freezing chamber space 9 provides for a continuous overflow of the gas atmosphere in the freezing chamber over its upper edge so that admission of surrounding air into the cold space is precluded.

As shown in FIG. 2, in an alternative embodiment, the carrier arm 2 may be divided into two parallel partial arms 17 in the section where it penetrates the wall 16 of the freezing chamber 6. The partial arms 17 each are separately inserted through vertical slot openings 18 into the freezing chamber wall 16 and join together at the specimen carrier 3 in the freezing chamber space 9. The partial arms 17 provide a pair of narrow, rectangular, vertically aligned sections and conform therefore to the shape of the slit opening 18. The distance from the sides of the carrier arm to the face of the opening 18 may be up to about 10 mm, preferably less than about 4 mm, and optionally less than about 1 mm, forming in this way a narrow air slot 20, visible in FIG. 2. The air slot is shown significantly larger than in actuality to provide here better depiction. The vertical height of the slot opening 18 is configured in such way that it will just allow for the swivel movement of the carrier arm 2.

In the embodiment displayed in FIG. 2, escape of gaseous nitrogen from inside the freezing chamber room 9 is reduced by throttling in the narrow air slit 20 as well as by significantly reduced individual diameter of the slit opening 18 on its upper and lower ends in comparison to a single opening.

Figure 3:
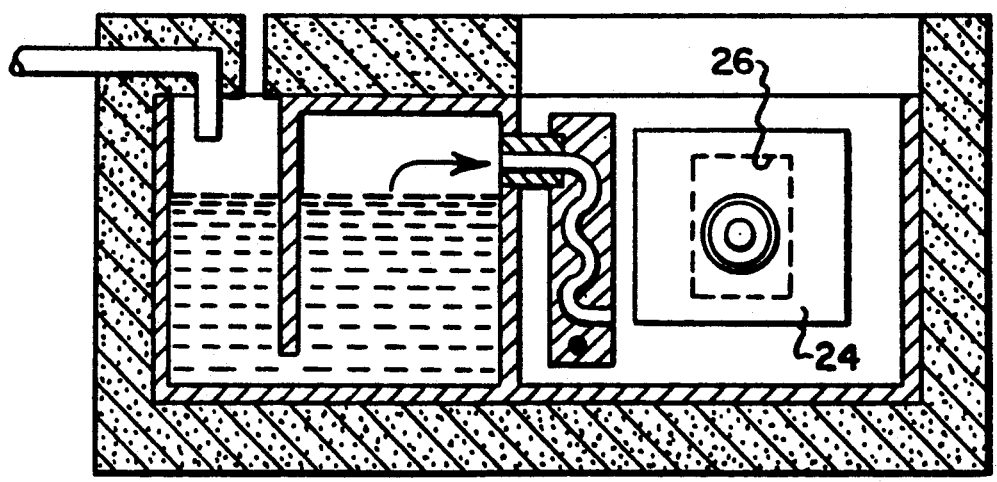
FIG. 3 is a view similar to FIG. 2 illustrating another embodiment of the inlet for a conventional carrier arm through the chamber wall.
Figure 4:
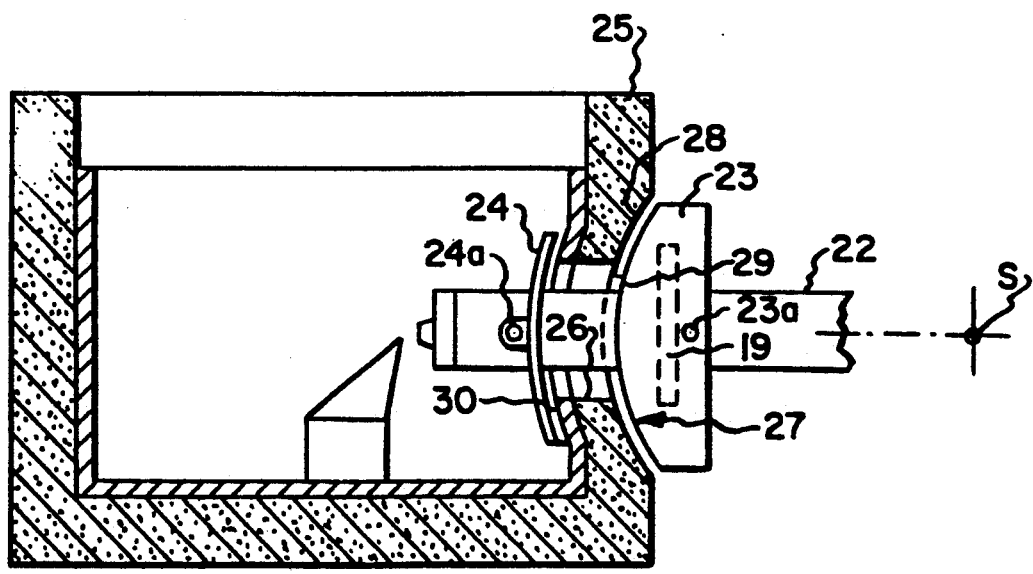
FIG. 4 is an enlarged side view of a freezing chamber of the embodiment illustrated in FIG. 3.

In FIGS. 3 and 4, only the parts important for the invention of the ultramicrotome are shown; the remaining ultramicrotome components can be assembled in the same way as shown in FIG. 1. With regard to the embodiment shown in FIGS. 3 and 4, the surface of the carrier arm 22 may be effectively extended by affixing disc-like elements 23 and 24 onto the carrier arm 22 on the outside and inside, respectively, of the chamber. The disc-like elements 23 and 24 extend radially outwardly from the carrier arm 22 and are positioned sufficiently close to the freezing chamber wall 25 to effectively enclose the opening 26. The carrier arm 2 is generally of a cylindrical cross-section, as shown in FIG. 3. The slot in the freezing chamber wall through which the cylindrical carrier arm penetrates is therefore an elongated slot having hemi-cylindrical upper and lower end surfaces. The outside disc element 23 may either consist of a good heat conducting material, such as that which is used to insulate the freezing chamber, or alternatively it may have an appropriate heat insulating layer applied on its backside.

The surface 27 of the disc element which faces the freezer chamber element has the shape of a convex cylindrical surface, the deflection axis corresponding to the swivel axis S of the carrier arm 22. In the area adjacent to the disc element 23, the freezing chamber 25 is concave shaped complementary to the convex curvature of surface 27, forming a concave surface 28. The surfaces 27 and 28 determine between each other a consistent width air slot 29, preferably less than 1 mm in width.

Inside the freezing chamber wall 25 a second disc element 24 is located which also consists of good heat conducting material, such as copper. The surface of the disc element 24 facing the freezing chamber wall 25 is a concave cylindrical shaped surface with the swivel axis S as deflection axis. The adjacent area of the freezing chamber wall 25 is shaped convex and complimentary to the concave surface of the disc element 24, so that between the facing surfaces, an air slit 30 of consistent width, less than about 5 mm and preferably less than about 1 mm, is maintained. Disk elements 23 and 24 are preferably constructed to be slidably mounted on specimen arm 22 with a device such as a set screw 23a and 24a, to enable adjustment of the gap by adjusting the position of disk elements 23 and 24.

Although the cross section of the carrier arm 22 is circular and the opening 26 provided in the chamber wall 25 is illustrated as rectangular (see FIG. 3), escape of nitrogen from inside the freezing chamber through opening 26 can be almost completely prevented by the disc elements 23, 24 and the respective surface of the chamber wall 25 which shape the slots 29 and 30 of significant length and relatively high flow resistance. Even less cryogen escapes if the top and bottom ends of opening 26 are hemi-cylindrical.

Figure 5A:
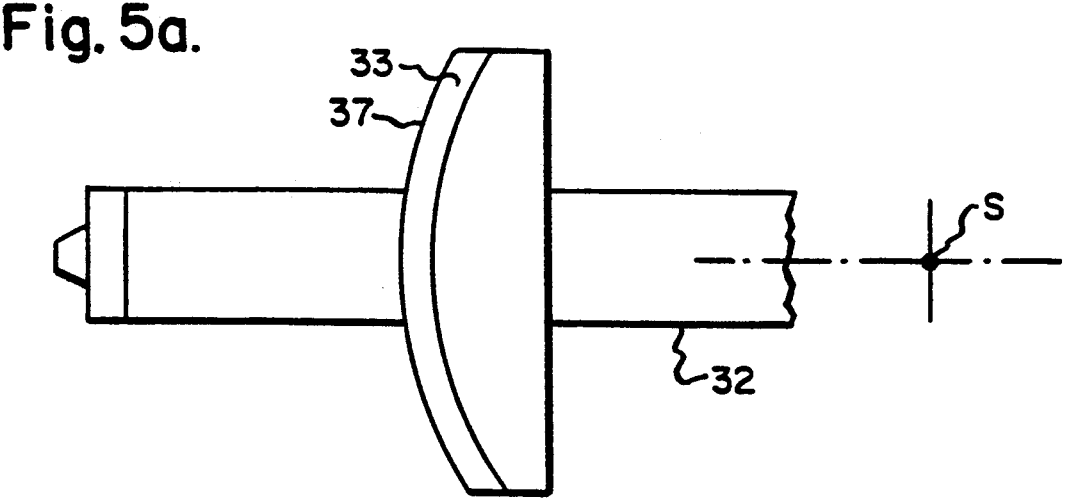
FIG. 5a is a side view of a third embodiment of carrier arm.
Figure 5B:
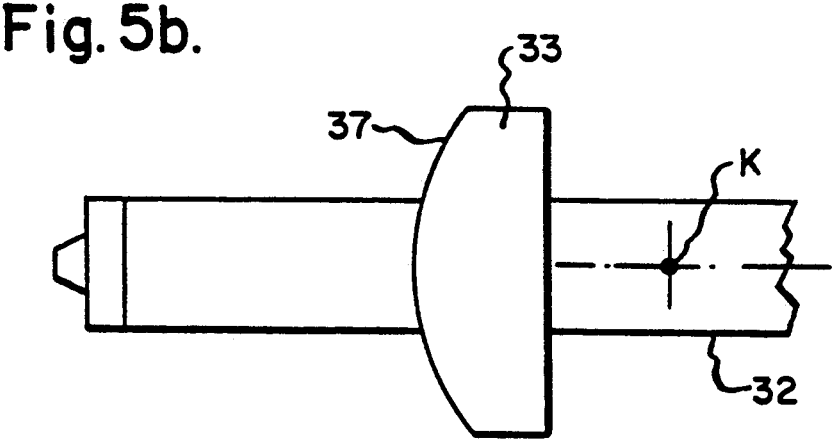
Figure 6:
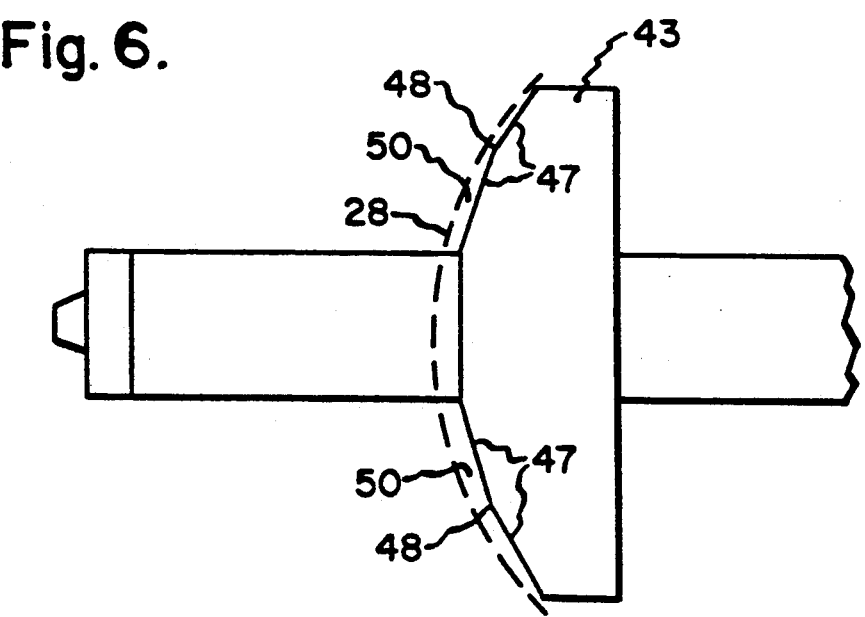
FIG. 6 is a side view of a fourth embodiment of carrier arm.

FIGS. 5 and 6 show modifications of the disc element 23 described above. In FIG. 5a, a spherically shaped surface 37 is provided on the disc element 33, facing the freezing chamber wall. The curvature of the surface 37 in the vertical direction has a radius corresponding to that which would occur via a rotation about the point S of the carrier arm 32. In the horizontal direction, the curvature of the surface 37, which is illustrated in FIG. 5b, has however a stronger curvature; its curvature has a radius corresponding to a rotation about point K on the carrier arm. Thus, the air slit obtained with the disc element 33 is longer for the same relative size of disc element, for example in comparison with the air slit 29 illustrated in FIGS. 3 and 4. The sealing effectiveness is further increased.

In FIG. 6, which is slightly enlarged for better comparison with drawing FIG. 5, the disc element provided on the carrier arm includes a surface 47 which faces the chamber wall, and which is substantially cylindrical in shape, the radius of curvature corresponding to that which results from a rotation about a point S on the carrier arm. However, the surface does not provide for a consistent radius, but instead is a polygonal surface. As shown in FIG. 6., between these flat surfaces of the polygon there exist corners 48. If the disc element 43 is employed in conjunction with a cylindrical surface 28 at the rear side of a freezing chamber wall 25, such as illustrated in FIGS. 3 and 4, an air slit is shaped which first widens and eventually narrows down again as shown in FIG. 6. The expanding spaces 49 are formed adjacent the flat polygon surfaces and the respective freezing chamber wall whereas the narrow spaces of the air slit 50 are formed adjacent the corners 48. An air slit design such as this causes increase resistance to flow, which in turn reduces the loss of cryogen.

As illustrated in FIG. 4, in order to maintain disc elements at a constant temperature, a heating device 19 may be embedded within the disc element 23.

What is claimed is:

1. In combination, a microtome and cryogen freezing chamber: said microtome comprising: a frame, an elongated specimen arm, pivot means connecting one end of said specimen arm to said frame for limited vertical movement of said arm about a pivot axis, a specimen holder at the other end of said arm, and a baffle mounted on said specimen arm, said baffle having a baffle surface extending away from said specimen arm, said baffle surface being convex with a center of curvature on said pivot axis; and said freezing chamber comprising: at least one upwardly extending wall, an elongated slot extending through said wall and defining two vertically-aligned, opposing wall surfaces, each of said wall surfaces being in close proximity to said arm, and said baffle surface being in close proximity to said wall and of a size to effectively close said slot, whereby the escape of cryogen is reduced.

2. The combination according to claim 1, wherein said convex surface is cylindrical.

3. The combination according to claim 1, wherein said wall has an outer surface and said outer surface has a concave portion surrounding said slot.

4. The combination according to claim 3, wherein said concave portion compliments said baffle surface.

5. The combination according to claim 4, further including means to selectively position said baffle along said arm.

6. The combination according to claim 3, further including another baffle mounted on said specimen arm, said another baffle having another baffle surface, said another baffle surface extending away from said specimen arm in close proximity to an inner surface of said wall.

7. The combination according to claim 6, wherein said another baffle surface is concave with a center of curvature on said pivot axis.

8. The combination according to claim 7, wherein said concave surface is cylindrical.

9. The combination according to claim 8, wherein said inner surface has a convex portion surrounding said slot, said baffle surface is spaced less than about 1 mm. from said concave portion, said other baffle surface is spaced less than about 1 mm. from said convex portion.

10. The combination according to claim 9, wherein said concave portion compliments said baffle surface and convex portion compliments said another baffle surface.

11. The combination according to claim 10, wherein said convex portion, concave portion, baffle surface and another baffle surface are each cylindrically curved about a vertical axis, said vertical axis being aligned perpendicular to said pivot axis to provide crossed-cylinder curvature and further including means to selectively position said baffle and said another baffle along said arm.

12. The combination according to claim 11 wherein said vertical axis is positioned between said pivot axis and said freezing chamber.

13. In combination, a microtome and cryogen freezing chamber: said microtome comprising: a frame, an elongated specimen arm, pivot means connecting one end of said specimen arm to said frame for limited vertical movement of said arm about a pivot axis, a specimen holder at the other end of said arm, and a baffle mounted on said specimen arm, said baffle having a baffle surface extending away from said specimen arm, said baffle surface being concave with a center of curvature on said pivot axis; and said freezing chamber comprising: at least one upwardly extending wall, an elongated slot extending through said wall and defining two vertically-aligned, opposing wall surfaces, each of said wall surfaces being in close proximity to said arm, and said baffle surface being in close proximity to said wall and of a size to effectively close said slot, whereby the escape of cryogen is reduced.

14. The combination according to claim 13, wherein said concave surface is cylindrical.

15. The combination according to claim 14, wherein said wall has an inner surface and said inner surface has a convex portion surrounding said slot.

16. The combination according to claim 15, wherein said convex portion compliments said baffle surface.

17. The combination according to claim 16 further including means to selectively position said baffle along said arm.

18. In combination, a microtome and cryogen freezing chamber: said microtome comprising: a frame, an elongated specimen arm having an elongated arm slot extending vertically therethrough to provide two arm portions, pivot means connecting one end of said specimen arm to said frame for limited vertical movement of said arm about a pivot axis, a specimen holder at the other end of said arm, and a baffle mounted on said specimen arm, said baffle having a baffle surface extending away from said specimen arm; and said freezing chamber comprising: at least one upwardly extending wall, an elongated wall slot extending through said wall, said wall slot being divided by a vertically extending wall bridge into two slot portions, each said slot portion having two vertically-aligned, opposing wall surfaces, one of said two arm portions extending through one of said two slot portions, and the other of said two arm portions extending through the other of said two slot portions, each of said wall surfaces being in close proximity to said arm, and said baffle surface being in close proximity to said wall and of a size to effectively close said wall slot, whereby the escape of cryogen is reduced.

* * * * *